US00PP09558P

United States Patent [19]

VandenBerg

[11] Patent Number: Plant 9,558

[45] Date of Patent: May 21, 1996

[54] CHRYSANTHEMUM PLANT NAMED 'SOPHIA'

[75] Inventor: Cornelis P. VandenBerg, Salinas, Calif.

[73] Assignee: Yoder Brothers, Inc., Barberton, Ohio

[21] Appl. No.: 366,476

[22] Filed: Dec. 30, 1994

[51] Int. Cl.[6] ..... A01H 5/00

[52] U.S. Cl. ..... Plt./76

[58] Field of Search ..... Plt./76, 80, 81

[56] References Cited

U.S. PATENT DOCUMENTS

P.P. 4,686 4/1981 Herrera et al. ..... Plt./76

P.P. 6,920 7/1989 Fuess ..... Plt./76

*Primary Examiner*—Howard J. Locker

*Attorney, Agent, or Firm*—Foley & Lardner

[57] ABSTRACT

A Chrysanthemum plant named Sophia particularly characterized by its flat capitulum form; decorative capitulum type; light purple ray floret color; diameter across face of capitulum of 50 to 60 mm when fully opened; spreading branching pattern; natural season flower date of September 20 to 30 when planting rooted cuttings on June 11 to June 18 in Hightstown, N.J.; plant height of 25 to 28 cm when grown in fall under natural daylength with no growth regulators in New Jersey; excellent uniform growth habit; and good flexibility of plant for handling, packing and shipping.

3 Drawing Sheets

The present invention comprises a new and distinct cultivar of Chrysanthemum, botanically known as *Dendranthema grandiflora,* and referred to by the cultivar name Sophia.

Sophia, identified as 8086 (89-709002), was originated from an open pollination of parents selcted by Cornelis P. VandenBerg in a controlled breeding program in Salinas, Calif., in 1988.

The female parent of Sophia was an unnamed seedling identified as 8395 (86-474001) and described as a flat decorative garden mum with many disc florets and with a bronze ray floret color.

The male parent of Sophia was unknown, since the breeding program consisted of open pollinated females.

Sophia was discovered and selected as one flowering plant within the progeny of the stated cross by Cornelis P. VandenBerg in September 1989, in a controlled environment in Salinas, Calif.

The first act of asexual reproduction of Sophia was accomplished when vegetative cuttings were taken from the initial selection in November 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Sophia are firmly fixed and are retained through successive generations of asexual reproduction.

Sophia has not been observed under all possible environmental conditions. The phenotype may vary significantly with variations in environment such as temperature, light intensity and daylength, without, however, any variance in genotype.

The following observations, measurements and comparisons describe plants grown in controlled open areas in Hightstown, N.J. Rooted cuttings were established in soil and maintained outdoors under the natural temperature and daylength prevailing during June through October.

The following traits have been repeatedly observed and are determined to be basic characteristics of Sophia, which, in combination, distinguish this Chrysanthemum as a new and distinct cultivar:

1. Flat capitulum form.
2. Decorative capitulum type.
3. Light purple ray floret color.

4. Diameter across face of capitulum of 50 to 60 mm when fully opened.
5. Branching pattern is spreading.
6. Natural season flower date of September 20 to 30 when planting rooted cuttings on June 11 to June 18 in Hightstown, N.J.
7. Plant height of 25 to 28 cm when grown in fall under natural daylength with no growth regulators in New Jersey.
8. Excellent uniform growth habit.
9. Good flexibility of plant for handling, packing and shipping.

The accompanying photographic drawings show typical inflorescence and leaf characteristics of Sophia, with the colors being as nearly true as possible with illustrations of this type.

Sheet 1 is a color photograph of Sophia grown as a pinched garden mum under natural season outside conditions in Salinas, Calif. Plants were grown outside and jug and transplanted into 15 cm pots at flowering time for photography purposes.

Sheet 2 is a black and white photograph of three views of the inflorescence of Sophia.

Sheet 3 is a black and white photograph showing the upper and under sides of the leaves of Sophia at three stages of development (mature, intermediate and immature).

In sheets 2 and 3 a measuring tape in centimeters has been added.

Of the commercial cultivars known to the inventor, the most similar in comparison to Sophia is the cultivar Lynn, disclosed in U.S. Plant Pat. No. 8,171. Reference is made to attached Chart A, which compares certain characteristics of Sophia to the same characteristics of Lynn.

Similar traits are capitulum form and type, although Lynn has a more formal flower form than Sophia. Diameter of capitulum of Sophia and Lynn is comparable. The color of both Sophia and Lynn is purple. However, Lynn shows a darker center of the flower, creating a two-tone effect, while Sophia does not show a darker flower center. Lynn has a more spreading plant habit and is generally taller when compared with Sophia. Sophia flowers 6 to 10 days earlier than Lynn.

In comparison to the cultivar Pink Champagne, disclosed in U.S. Plant Pat. No. 6,920, Sophia has a smaller diameter of capitulum (5–6 cm. compared to 6–8 cm. for Pink Champagne), a shorter, more compact plant habit with more spread, and a 14 day earlier flowering date in California. When grown in New Jersey, both cultivars had comparable flowering dates.

In the following description, color references are made to The Royal Horticultural Society Colour Chart. The color values were determined on plant material grown as a pinched garden mum grown outdoors in Salinas, Calif., on Aug. 21, 1994.

Classification:

*Botanical.*—*Dendranthema grandiflora,* cv., Sophia.

*Commercial.*—Flat decorative garden mum.

INFLORESCENCE

Capitulum:

*Form.*—Flat.

*Type.*—Decorative.

*Diameter across face.*—50 to 60 mm when fully opened.

Corolla of ray florets:

*Color (general tonality from a distance of three meters).*—Light purple.

*Color (upper surface).*—75A. Outer petals fade to 75C to 75D.

*Color (under surface).*—Base 75C, apex 75B.

*Shape.*—Cross section convex, longitudinal section straight.

Corolla of disc florets:

*Color (mature).*—14A.

*Color (immature).*—14A, tinged with 144C.

Reproductive organs:

*Androecium.*—Present on disc florets only, very few; scant pollen.

*Gynoecium.*—Present on both ray and disc florets.

PLANT

General appearance:

*Height.*—25 to 28 cm when grown in fall under natural daylength with no growth regulators in New Jersey.

*Branching pattern.*—Spreading.

Foliage:

*Color (upper surface).*—147A.

*Color (under surface).*—147B.

*Shape.*—Deeply lobed, serrated.

CHART A

| | SOPHIA | LYNN |
|---|---|---|
| Ray floret color | Light purple | Light purple |
| Capitulum form and type | Flat, decorative | Flat, decorative |
| Diameter across face of capitulum | 50 to 60 mm | 51 to 60 mm |
| Branching pattern | Spreading | Spreading and prolific |
| Natural season flower date in Hightstown, NJ | Sept. 20 to 30 | Sept. 26 to Oct. 10 |
| Plant height in natural season fall | 25 to 28 cm | 25 to 33 cm |

COMPARISONS MADE OF PLANTS GROWN UNDER NATURAL SEASON OUTDOOR CONDITIONS HIGHTSTOWN, NEW JERSEY

It is claimed:

1. A new and distinct Chrysanthemum plant named Sophia, as described and illustrated.

* * * * *

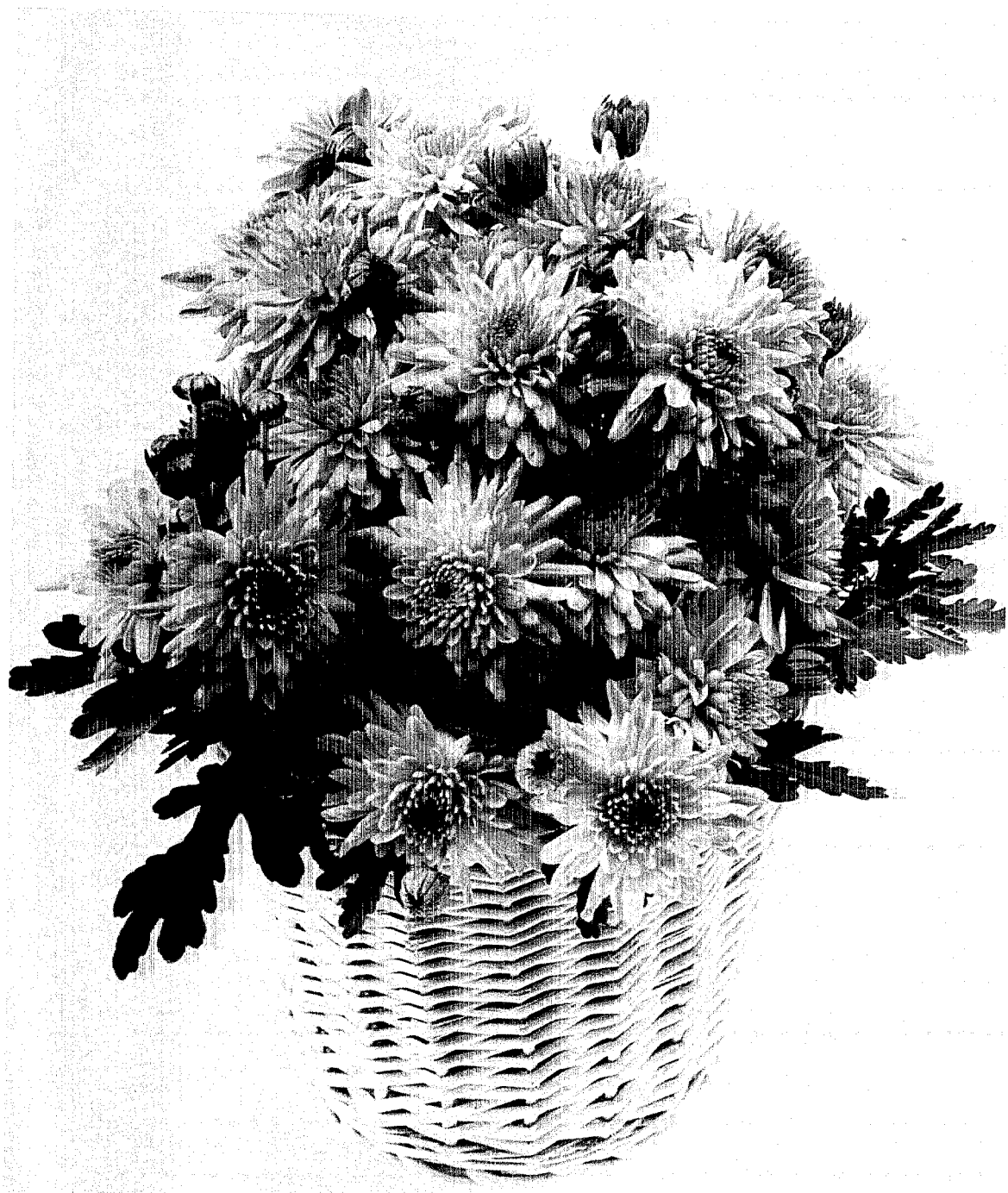

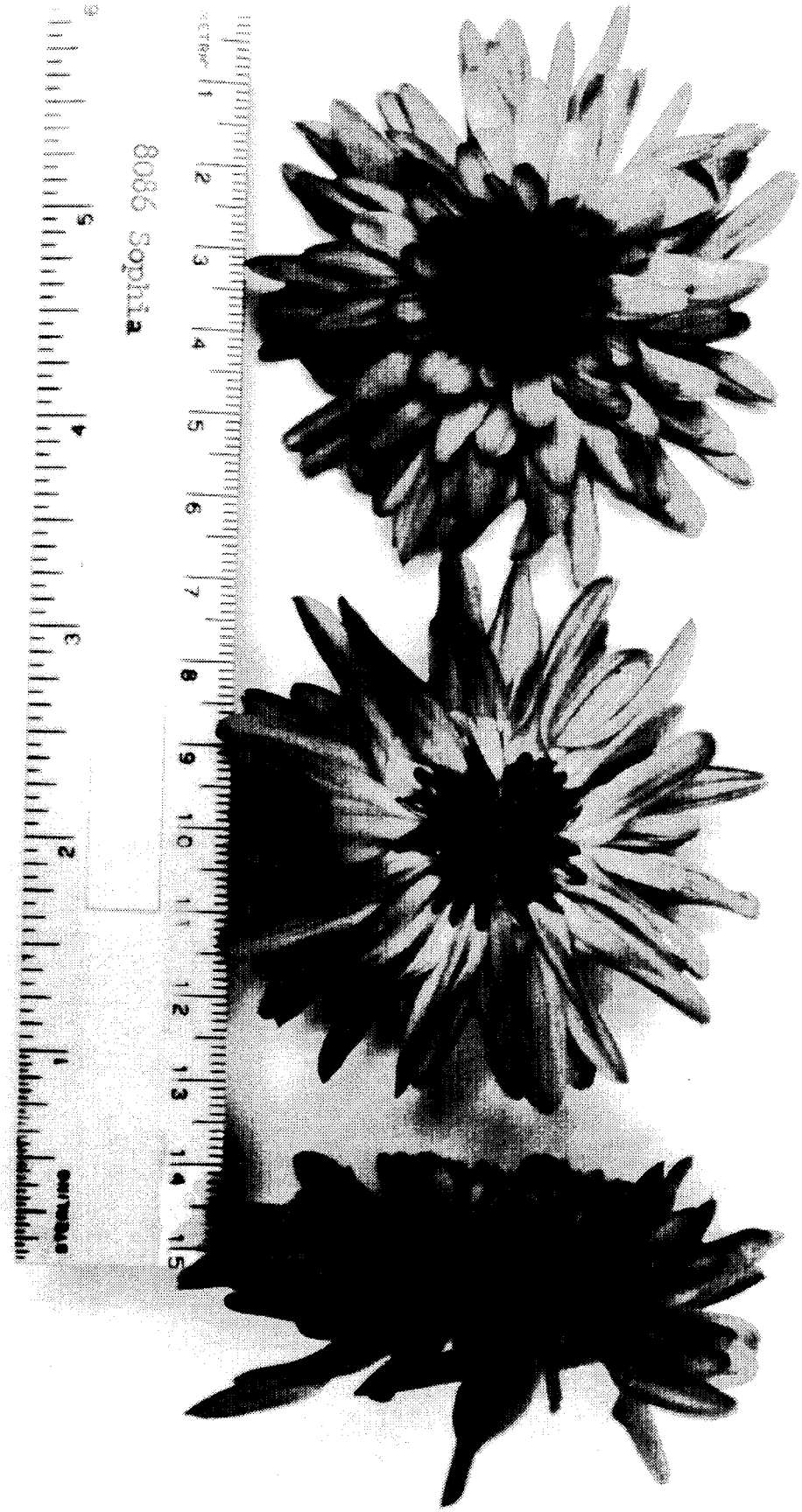
8086 Sophia

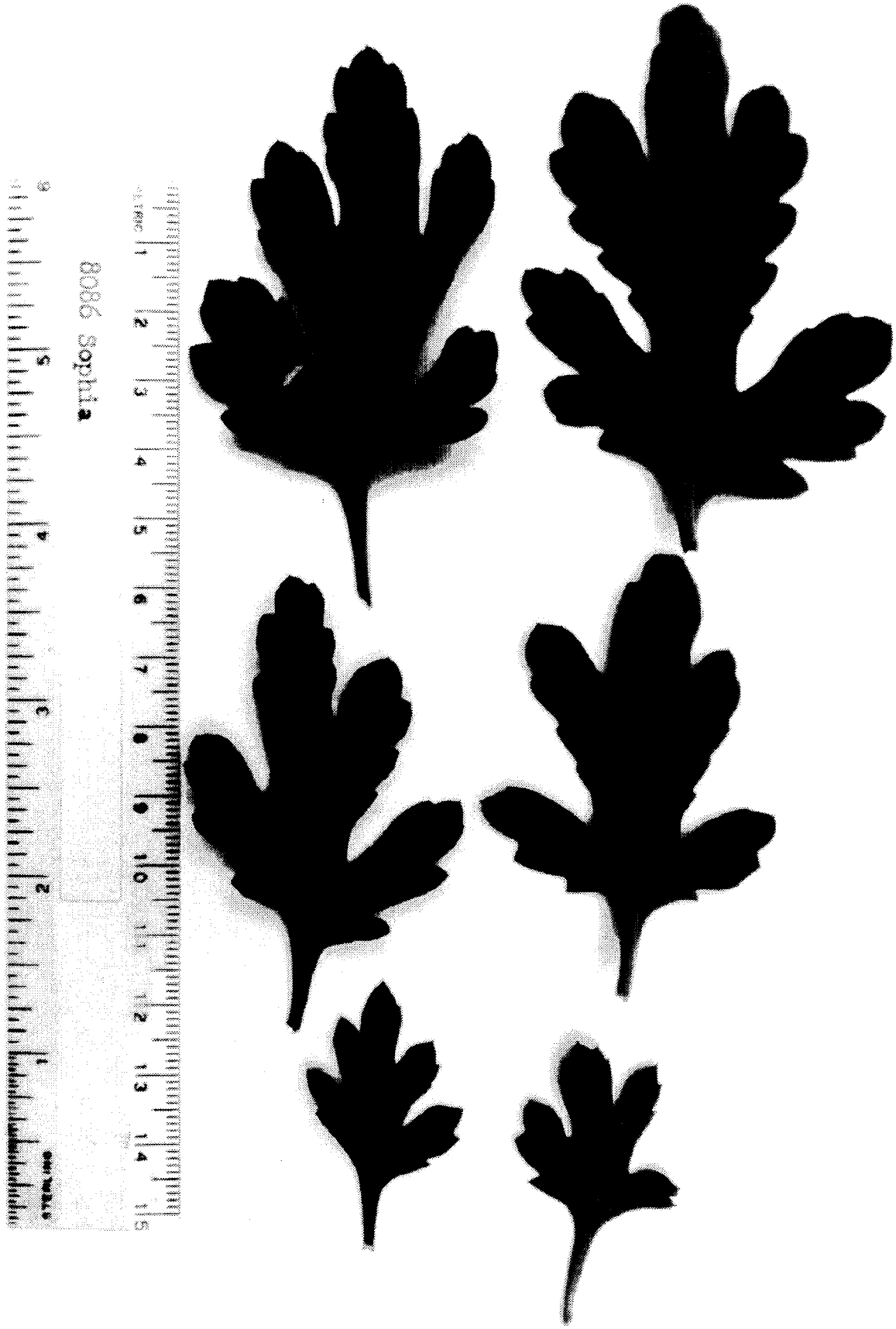
8886 Sophia